United States Patent [19]

Siegell

[11] 4,443,231
[45] Apr. 17, 1984

[54] CONTINUOUS CHROMATOGRAPHIC SEPARATIONS IN A MAGNETICALLY STABILIZED FLUIDIZED BED

[75] Inventor: Jeffrey H. Siegell, Westfield, N.J.

[73] Assignee: Exxon Research and Engineering Co., Florham Park, N.J.

[21] Appl. No.: 345,095

[22] Filed: Feb. 2, 1982

[51] Int. Cl.³ .......................................... B01D 15/08
[52] U.S. Cl. .......................................... 55/3; 55/67; 55/100; 55/386
[58] Field of Search .................. 55/3, 67, 100, 147, 55/386, 390; 210/661, 656, 695, 198.2

[56] References Cited

U.S. PATENT DOCUMENTS

| | | | |
|---|---|---|---|
| 1,291,137 | 1/1919 | Reed | 209/474 |
| 3,078,647 | 2/1963 | Mosier | 55/197 |
| 3,236,092 | 2/1966 | Carter | 55/67 |
| 3,264,801 | 8/1966 | Buhl et al. | 55/67 |
| 3,482,376 | 12/1969 | Tuthill | 55/197 |
| 3,527,350 | 9/1970 | Tuthill | 210/198.2 |
| 3,843,518 | 10/1974 | Magee et al. | 55/67 |
| 4,132,005 | 1/1979 | Coulaloglou | 34/10 |
| 4,247,987 | 3/1981 | Coulaloglou | 55/100 X |
| 4,254,556 | 3/1981 | Mayer | 55/100 |
| 4,283,204 | 8/1981 | Savage | 55/3 |

Primary Examiner—John Adee
Attorney, Agent, or Firm—John W. Ditsler

[57] ABSTRACT

A multicomponent feed mixture may be separated into its components continuously by injecting said feed mixture and a carrier fluid into a magnetically stabilized fluidized bed containing adsorbent particles admixed or composited with magnetizable particles. The bed particles continuously move transverse to the flow of the carrier fluid, which serves to fluidize the bed, such that the components of the feed mixture are transported downstream varying distances from the injection point depending upon the adsorption and desorption characteristics of said components. Product streams comprising a portion of the carrier fluid and a portion of the feed mixture containing at least a portion, preferably a major portion, of one of the components can then be recovered from the surface of the bed, the most strongly adsorbed component being transported (and thus recovered) farthest from the injection point.

35 Claims, 11 Drawing Figures

CONTINUOUS CHROMATOGRAPHIC SEPARATIONS IN A MAGNETICALLY STABILIZED FLUIDIZED BED

FIELD OF THE INVENTION

The present invention relates to the separation of a feed mixture using a magnetically stabilized fluidized bed. More particularly, the invention concerns a process for the continuous chromatographic separation of a multicomponent feed by contacting said feed with solids having adsorptive properties which move transverse to the flow of the fluidizing fluid in a magnetically stabilized fluidized bed.

BACKGROUND OF THE INVENTION

In conventional chromatographic processes, a pulse of a feed mixture and a continuously flowing carrier fluid are introduced into a column packed with an adsorbent. The adsorbent is usually a porous or granular solid or an inert granular material on which there has been deposited a film or coating of a desired nonvolatile liquid adsorbent. The components of the feed mixture pass through the column with the carrier fluid at different velocities which are dependent upon the respective affinity of each component with the adsorbent. Therefore, each component of the feed mixture will be retained by the adsorbent for a time which is characteristic to it and will exit from the column with the carrier fluid at different times, the components of the feed that are least adsorbed in the column exiting first.

Normally, conventional chromatographic processes are conducted as batch operations. However, numerous attempts have been made to effect chromatographic separation of a multicomponent feed continuously (see Sussman, M. V. and N. S. Rathore, *Chromatographia*, Vol. 8, February 1975; Rendell, M., *Process Engineering*, April 1975; and Sussman, M. V., *Chemtech*, April 1976). One of the earliest techniques suggested involved filling the annular space between two concentric cylinders with adsorbent and passing the feed mixture and carrier gas through the adsorbent axially as the annulus rotated slowly (see Martin, A. J. P., *Disc. Faraday Soc.*, Vol. 7, p. 332 (1949)). Another technique required a Gatling gun arrangement of vertical columns in a circle (see Svensson et al, *Science Tools*, 2, (2), p. 17 (1955). While several variations of the rotating annulus configuration have been suggested (see, for example, U.S. Pat. Nos. 3,187,486; 3,257,781; 3,511,028; 3,732,982; Dinelli, D. M. et al., *J. Chromatography*, 7, 442 (1962); Polezzo, S. and M. Taramasso, *J. Chromatography*, 11, 19 (1963); Taramasso, M. and D. M. Dinelli, *J. Gas Chromatography*, 2, 150 (1964); Wankat, P. C. et al, *I&E.C. Fund.*, 15, No. 4 (1976); Scott, C. D., et al., *J. Chromatography*, 26 (1976)), all are mechanically complicated and cumbersome due to the difficulty in rotating the large number of tubes or the bed of solids. In addition, the efficiency of such devices is limited because, as in conventional packed chromatographic columns, reducing the particle size of the adsorbent causes an increased pressure drop in the column.

Several other geometries have been suggested for effecting continuous multicomponent separations. For example, U.S. Pat. No. 3,078,647 discloses a packed bed annular system wherein the feed mixture and carrier gas flow radially from the inner to the outer cyclinder while the cylinders rotate (see also U.S. Pat. No. 3,527,350).

As another example, U.S. Pat. No. 3,503,712 discloses a system wherein two rotating discs are placed close together, each disc being coated with a thin layer of adsorbent solvent. No solid adsorbent is packed between the discs. Carrier fluid is injected at the center of the discs and flows in the radial direction while feed is introduced at a single point such that transverse flow will occur due to the angular motion of the discs and the radial flow of the carrier fluid. Yet another approach involves the alternate continuous injection of two carrier fluids into a rectangular slab packed with adsorbent, the flow of each carrier fluid being perpendicular to the flow of the other, such that the components in the continuously injected feed are separated as the direction of fluid flow changes at right angles while changing the temperature (see U.S. Pat. No. 3,482,376 and Tuthill, E. J., *J. Chrom. Sci.*, 8 (1970)). However, packed bed arrangements suffer from the pressure drop limitation mentioned previously while disc systems are limited to handling low capacities.

SUMMARY OF THE INVENTION

Accordingly, the present invention relates to obtaining continuous chromatographic separations without the limitations and disadvantages of the prior art by use of a magnetically stabilized fluidized bed. More specifically, a multicomponent feed may be separated into its components continuously by injecting said feed and a suitable upward moving carrier fluid into a magnetically stabilized fluidized bed containing magnetizable particles admixed or composited with adsorbent particles or material. The bed particles continuously move transverse (i.e., non-parallel) to the flow of the carrier fluid, which serves to fluidize the bed, such that the components of the feed mixture are transported downstream varying distances from the injection point depending upon their adsorption and desorption characteristics. Product streams comprising a portion of the carrier fluid and at least a portion, preferably a major portion, of at least one of the feed components can then be recovered from the surface of the bed, the most strongly adsorbed component being transported (and thus recovered) furthest from the injection point. More preferably, each product stream will comprise a portion of the carrier fluid and a portion of said feed mixture consisting essentially of one of said components.

The fluidized bed is stabilized by a magnetic means (i.e. a magnetic stabilizing means), which should be of sufficient strength to suppress particle backmixing within the bed but below that which would cause excessive particle to particle attractive forces. Similarly, the superficial velocity of the fluidizing fluid (i.e. carrier fluid) should be in excess of the normal minimum fluidization superficial velocity in the absence of magnetic effects, but below the superficial velocity which will cause solids backmixing.

DETAILED DESCRIPTION OF THE INVENTION

The present invention is based upon an improved chromatographic method for continuously separating a multicomponent feed comprising two or more components into two or more streams which have chemical compositions of reduced complexity. Since there are no moving mechanical parts (i.e., the solids are the only moving part), the disadvantages inherent in many of the chromatographic techniques heretofore proposed are avoided. Accordingly, a multicomponent feed comprising at least two components is continuously introduced into a continuously moving bed of adsorbent particles admixed or composited with magnetizable particles under fluidization conditions wherein said bed is stabilized by a magnetic means. Bed fluidization is achieved by contact with an upward moving carrier fluid which passes transverse to the flow of said bed particles. The carrier fluid may be either gaseous or liquid. Utilization of an adsorbent which has a different affinity for each of the components of the feed mixture will result in the components being transported through the bed by the carrier fluid at rates which are dependent upon the affinities of the adsorbent for each component. Thus, separation of the components of the feed mixture is obtained by the differential rate of adsorption and desorption of the adsorbant for each component. Product streams, in a number corresponding to the number of fractions to be separated from the feed mixture, are withdrawn at spaced locations along the course of the moving adsorbent and carrier fluid. Typically, each product stream is withdrawn from the upper surface of the bed although a stream could be withdrawn from the bed at another location. Each of the product streams will comprise a portion of the carrier fluid and a portion of the feed mixture containing at least a portion, preferably a major portion, of one of the components of the feed. More preferably, the product stream will comprise a portion of the carrier fluid and a portion of the feed mixture consisting essentially of one of the components of said feed mixture.

Each of the product streams withdrawn from the magnetically stabilized fluidized bed may then be introduced into a suitable means for separating the carrier fluid therefrom. Suitable means include, but are not limited to, coolers for condensing the desired product from the carrier fluid, distillation for separation by volatility, and adsorption or chromatographic columns for separation by adsorbtivity.

The present invention may be used to separate virtually all substances inherently capable of being separated chromatographically. For example, liquid mixtures, as well as gas mixtures, may be separated. Components of the feed mixture may be selected from the group consisting of hydrocarbons, non-hydrocarbons and mixtures thereof. The hydrocarbon components will have at least 1 carbon atom per molecule, typically from 1 to 30 carbon atoms per molecule, and will include mixtures of hydrogen gas and hydrocarbons. Illustrative of hydrocarbon groups that can be separated according to the present invention include alcohols, aromatics, esters, ethers, halogenated hydrocarbons, ketones, olefins, paraffins and the like. Specific examples of suitable hydrocarbon components are methane, ethane, ethylene, propane, butane, butene, butadiene, pentane, hexane, heptane, octane, nonane, decane, dimethy-butane, dimethyl-pentane, trimethyl-pentane, and other normal aliphatic hydrocarbons and their isomers; cyclohexane, decaline, tetraline and other alicyclic-hydrocarbons; benzene, toluene, xylene, diethylbenzene, ethyl-toluene, trimethyl-benzene, butyl-benzene and other aromatic hydrocarbons such as alkyl benzene, or alkyl-naphthalene; industrial product of hydrocarbon mixtures of paraffin, naphtha or reformate; pyrogasoline and other hydrocarbon derivatives from naphtha cracking process and those products yielded from distillation, alkylation or hydration processes. Both hydrocarbon mixtures comprising two or more compounds of different molecular weights, as well as the same molecular weights, that is, isomers, may be included as a feed mixture. Examples of isomer mixtures are $C_5$ aliphatic isomers of dimethylpropane and pentane; $C_6$ aliphatic isomers of dimethylbutane, ethylbutane, methylpentane and hexane; $C_7$ aliphatic isomers of dimethyl-pentane, methylhexane and heptane; $C_8$ aliphatic isomers of trimethylhexane and octane, $C_8$ alicyclic isomers of dimethylcyclohexane and ethylcyclohexane. The present invention is particularly suited for separating aromatic compounds; for example separating paraxylene from an admixture of ethyl benzene, ortho-, meta-, and paraxylenes as is disclosed at columns 27-28 of U.S. Pat. No. 4,247,987, the disclosure of which is incorporated herein by reference. Straight chain paraffins from recycle streams in $C_5/C_6$ recycle isomerization units can also be separated according to the present invention. Another suitable feed is a $C_9-C_{18}$ hydrocarbon fraction and more preferably $C_{10}-C_{15}$ kerosene fraction. The feed mixture may contain normal paraffins, isoparaffins and aromatics in varying concentrations, depending on the type of crude from which the hydrocarbon fraction is derived and the carbon number range of the fraction. The normal paraffin concentration will typically range from about 20 to about 60 vol. % of the mixture and the aromatic concentration will typically range from about 10 to about 30 vol. % of the mixture, although the precise content may vary from these values. The present invention is also suitable for separating the $C_4$ isomers of butane, 1-butene, 2-butene and butadiene as well as the ethane/ethylene mixture. The hydrocarbon product from a steam cracker can also be separated using the present invention.

The carrier fluid will be composed of at least one desorbent, alone or admixed with a chemically inert fluid. Criteria which will determine the composition of the carrier fluid and the concentration of the desorbent(s) therein will depend on fluid mechanic requirements and adsorption requirements of the process. For example, the carrier fluid will contain sufficient desorbent(s) at a specific concentration(s) so that the components of the feed mixture move in the direction of the carrier fluid toward the upper surface of the bed. In addition, other fluids may be mixed with the desorbent(s) fluid such that the superficial velocity of the carrier fluid is in excess of the normal minimum fluidization superficial velocity in the absence of magnetic effects, but below the superficial velocity which will cause solids backmixing.

For processes requiring only separations (i.e., not involving chemical reactions), the carrier fluid should be chemically inert with respect to the components being separated and the adsorbent. Examples of suitable carrier gases include nitrogen, steam, air, helium, hydrogen, argon, methane, carbon dioxide, and the like. Examples of suitable carrier liquids, particularly for the separation of $C_8$ aromatic isomers, include toluene, alkyl-substituted aromatic hydrocarbons having 7 to 12 carbon atoms and various paraffinic mixtures.

The particular adsorbent employed can vary broadly and will depend upon the components of the mixture to be separated. Inorganic, organic or high molecular weight inorganic or organic adsorbents may be used. Natural magnetite may also be used as an adsorbent in gas-solid chromatography (*Journal of Chromatography*, 172, 357–361 (1979)). In addition, the adsorbent may have catalytic properties.

Adsorbents suited for the present separation process include activated carbons, treated activated carbons, molecular-sieving carbon; selected artificially synthesized zeolites, such as those having some particular ratio of principal components identified as: "Type A", "Type L", "Type X", "Type Y", "Type ZSM", mordenite, faujasite, erionite, and the like; those zeolites which have a particular silica-alumina ratio and those in which the original sodium cations are exchanged to other cations; selected silica-gels such as those having some particular relative components of silica, alumina and ferric oxides, those which have particular steric properties as the average pore diameter, specific surface area, pore volume and others; selected activated alumina such as those having particular components of aluminum oxide and water, those hydrated forms, some particular crystal forms, those which have a particular structure; activated clay or selected acid clays such as montmorillonite in which case base is exchange holloysite or attapulgite.

Certain of the above adsorbents are particularly effective in separating specific components of a feed mixture. For example, silica gel is selective in removing aromatic hydrocarbons from non-aromatic hydrocarbons while activated carbons are useful in separating olefins from paraffins. In addition, zeolites which have a pore size of about 5 Å are utilized to separate small molecules such as n-paraffins to the substantial exclusion of other molecular species while zeolites which have a pore size of about 13 Å (the so called large pore zeolites such as "Type X", "Type Y" and "Type L") admit most of the components normally found in a process stream.

Most of the aforesaid adsorbents are readily available in the commercial market. Also the adsorbents similar to those which are commercially available can be, in general, synthesized without elaborate techniques. In addition many adsorbents can be prepared by chemically or physically treating commercially available adsorbents. A further description of the zeolites mentioned above and their methods of preparation are given, for example, in U.S. Pat. Nos. 2,882,243; 2,882,244; 3,130,007; 3,410,808; 3,733,390; 3,761,533; 3,827,968 and patents mentioned therein, the entire disclosures of which are incorporated herein by reference.

Another class of adsorbents include cation-exchange resins with exchange groups of benzene sulfonic acid, carboxylic acid, phosphoric acid; strongly or weakly basic anion-exchange resins; high molecular weight particles of styrene-divinylbenzene copolymer, or its halomethylated, or cyano-ethylated polymers; acrylonitrile copolymers; high molecular weight compounds having several functional groups such as cyano, cyanomethyl, chloromethyl, thioether, sulfone, isocyanate, thiocyanate, thiourea, allyl, acetylacetone, aldehyde, ketone, aliphatic, anhydride, ester, halogen, nitro and others.

The most suitable adsorbents for achieving high adsorption-desorption rates are synthetic zeolites, activated or treated carbon adsorbents and high molecular weight organic materials. These adsorbents generally show high exchange rate of adsorbing components, probably because of their chemical affinity for various contaminant substances such as acid gases and polar molecules, in the case of high molecular weight materials, and because of the macropores in case of synthetic zeolites which comprise minute crystals smaller than a few microns, and clay or other binding material.

Typical examples of suitable adsorbents are synthetic zeolite "Type A" for the separation of various polar molecules from gaseous feeds. Type A zeolite has a typical oxide formula $Na_2O.Al_2O_3.2SiO_2.41/2H_2O$, a typical unit-cell formula $Na_{12}[(AlO_2)_{12}(SiO_2)].27H_2O$, a density of 1.99 g/cc, a unit cell constant of 12.32–24.64 Angstroms, a void volume of 0.47 cc/cc, a free aperture of 2.2 Å($\beta$)–4.2 Å($\alpha$), and a kinetic diameter of 3.6–3.9 Å.

Synthetic zeolites are one of the most useful inorganic adsorbents because the adsorption power of polar molecules onto zeolites can easily be altered by exchanging sodium ions which usually come from the original production steps into some other cations to change their crystal structure or electron configurations to the desired forms. Usually Group I metal ions such as lithium, potassium, rubidium, cesium, silver, copper; Group II metal ions such as beryllium, magnesium, calcium, strontium, barium, zinc, cadmium, mercury, titanium, vanadium, chromium, nickel, cobalt, iron, manganese, rare earth metals, uranium, lead cations or their mixtures are used to replace sodium ions originally contained in the zeolites. The most effective sets of cations are: potassium and lithium; potassium and calcium, potassium and cadmium, potassium and iron; potassium and nickel, potassium and cobalt; potassium and barium, potassium and magnesium; calcium and magnesium; calcium and manganese, lithium and manganese, barium and sodium; barium and lead; iron and uranium; and others. Given a particular feedstream, the most suitable set of cations, their relative compositions, or most effective activation treatments can be easily selected through various experiments, since cation-exchange procedure is readily repeated many times. Generally, Type A synthetic zeolites are exchanged with calcium or magnesium or their mixtures for separating the straight chain hydrocarbons from branched chain hydrocarbons.

For separating $C_8$ aromatic mixtures and more particularly for separating paraxylene from a mixture of its isomers and/or ethylbenzene, Type X or Type Y crystalline aluminosilicates such as disclosed in U.S. Pat. Nos. 2,882,244; 3,130,007, 3,761,533 are preferred. A particularly preferred adsorbent for separation of $C_8$ aromatic mixture is the modified Type Y zeolite containing predominantly potassium ions and having a unit cell of 24.50 to 24.75 Angstroms, e.g., such as disclosed in U.S. Pat. No. 3,686,343, the entire disclosure of which is incorporated herein by reference.

Other sorbents have been idenitified for use in separating aromatic hydrocarbons. For example, silica gel sorbents are effective in separating aromatic hydrocarbons from hydrocarbon mixtures. U.S. Pat. No. 2,965,687 discloses the use of amine modified bentonite as a sorbent for separating aromatics and, in particular, for separating paraxylene from metaxylene. U.S. Pat. No. 3,114,782 teaches the use of calcium faujasite for the selective adsorption of metaxylene by a vapor phase treatment at about 350° F. with benzene as the desorbent, the metaxylene being sorbed preferentially in the calcium faujasite so that the paraxylene is controlled in the raffinate. Several related patents (U.S. Pat. Nos. 3,558,730; 3,558,732; 3,636,121 and 3,636,180) disclose methods of separating paraxylene by sorption onto a crystalline alumino silicate having a mixture of cations (e.g., barium and potassium) using elevated temperature, super-atmospheric pressures and process conditions for maintaining the xylene in the liquid state. A process with enhanced selectivity is described in U.S. Pat. No. 3,395,711; wherein a gaseous modifying agent, such as ammonia, is included. Separation of $C_8$ aromatics using ZSM-5 is also disclosed in U.S. Pat. Nos. 3,653,184; 3,656,278; 3,698,157; 3,724,170; 3,729,523; 3,760,024; 3,770,841 and 3,960,520, the entire disclosures of which (including the entire disclosure of all patents identified in this paragraph) are incorporated herein by reference.

The adsorbent particles may be used as admixtures or as composites with a ferromagnetic or ferrimagnetic substance. All ferromagnetic and ferrimagnetic substances, including, but not limited to, magnetic $Fe_3O_4$, $\gamma$-iron oxide ($Fe_2O_3$), ferrites of the form $MO.Fe_2O_3$, wherein M is a metal or mixture of metals such as Zn, Mn, Cu, etc.; ferromagnetic elements including iron, nickel, cobalt and gadolinium, alloys of ferromagnetic elements, etc., may be used as the magnetizable and fluidizable particulate solids which are used in admixture or composited with the adsorbent particles or material. Alternatively the adsorbent may itself contain a ferromagnetic or ferrimagnetic substance in its chemical or physical makeup. In this case, the adsorbent exhibits magnetic properties. Therefore, no additional magnetic material need be admixed or composited with the adsorbent. The non-ferromagnetic material may also have catalytic properties.

The solids used in the magnetically stabilized fluidized bed can be composited with or admixed with ion-exchange resins to effect typical ion-exchange separations including, but not limited to, water purification (e.g., removal of fluorides, nitrates, oxygen, ammonia, etc.), purification of solvents (e.g., alcohols, benzene, acetone, etc.), purification of reagents (e.g., hydrochloric acid, phenol, formaldehyde, acrylates), recovery and purification of metals (e.g., uranium, thorium, transition metals, gold, silver, platinum, etc.), purification of sugars and polyhydric alcohols, biological recovery and purification (e.g., antibiotics, vitamins, amino acids, proteins, etc.).

The composites of the magnetizable component and the adsorbent may be prepared by mixing the magnetic component, such as 400 Series stainless steel particles, and the adsorbent, e.g., the zeolite sieve, with a base for the adsorbent to form a relatively homogeneous gel. The adsorbent base may be comprised of, for example, silica, alumina or silica-alumina. The gel is then dried, calcined and sized. Suitable techniques for sizing and shaping the composite adsorbent are extrusion, pilling, beading, spray drying, etc. The magnetizable component may also be composited with the adsorbent by impregnation, cogelling, coprecipitation, etc. U.S. Pat. No. 4,247,987 also describes a method of preparing magnetizable sorption particles.

The bed particles (composites or admixtures) will typically have an average mean particle diameter ranging from about 50 to about 1500 microns, preferably from about 100 to about 1000 microns. The particles may be of a single size or a mixture of several size ranges. Similarly, the particles may be of any shape, e.g., spherical, irregular shaped or elongated, but substantially spherical particles are preferred.

The weight fraction of magnetizable component when admixed or composited with non-magnetic adsorbent particles or material will vary depending upon the particular components to be separated, the adsorbent employed, process conditions and the like. Typically, however, the fraction of magnetizable component in the bed will be at least 10 weight percent and, preferably, should range from about 25 to about 75 weight percent.

According to the present invention, the particles comprising the fluidized bed are subjected to a magnetic stabilizing means, which may be produced by a variety of methods. For example, the magnetic stabilizing means may be produced internally using permanently magnetized particles (such as are described in U.S. Pat. No. 4,261,101, the entire disclosure of which is incorporated herein by reference) or externally using an applied magnetic field. While the magnetic stabilizing means employed may be either internal or external (with external being preferred), the present invention will be described hereinafter with respect to the use of an externally applied magnetic field, most preferably a uniform applied magnetic field having a substantial component along the direction of an external force field (i.e., gravity).

The magnetically stabilized fluidized bed has been described as a quiescent, fluid-like bed which is totally free of bubbles or pulsations and which results when a uniform magnetic field is applied to a bed of magnetizable solids in a direction colinear with the flow of the fluidizing fluid (see Rosenweig et al, *AIChE Symposium Series*, 77, 205, p. 8-16 (1981), the entire disclosure of which is incorporated herein by reference). As such, magnetic stabilization produces a non-bubbling fluid state having a wide range of operating velocities between a lower limit given by the normal minimum fluidization superficial fluid velocity ($U_{mf}$) required to fluidize or levitate the bed of solids in the absence of the magnetic field and an upper limit given by the superficial fluid velocity ($U_T$) required to cause timevarying fluctuations of pressure difference through the stabilized fluidized bed portion during continuous fluidization in the presence of an applied magnetic field. The bed may also be operated within a narrower range substantially near the locus of transition between the bubbling and stabilized regimes of the bed as described for countercurrent magnetically stabilized beds in U.S. Pat. No. 4,247,987, the entire disclosure of which is incorporated herein by reference, and for transverse flow magnetically stabilized beds in copending application Ser.

No. 345,094 filed on the same date herewith such that the fluidity ratio or $(U_T-U_{op})/(U_T-U_{mf})$ ranges between $-0.1$ and $+0.5$ where $U_{op}$ is the actual operating superficial fluid velocity.

The fluidity of a magnetically stabilized bed continuously decreases from the fluidity at $U_T$ as the magnetic field is increased above, or the superficial fluid velocity is decreased below, the value at $U_T$. Transverse flowing stabilized beds which are operated further away from $U_T$ exhibit essentially plug flow; i.e., essentially a flat velocity profile. In contrast, transverse flowing stabilized beds which are operated close to $U_T$ exhibit a non plug flow solids velocity profile in the vertical direction and have increased fluidity. However, deviations from a plug flow profile when the beds are operated in the more fluid region may be reduced or substantially eliminated by proper design of a solids flow weir at the bed exit. Plug flow conditions are preferred for the practice of the present invention.

Magnetically stabilized fluidized beds have the appearance of expanded fixed beds with essentially no gross solids backmixing and essentially no fluid bypassing. The application of the magnetic field allows superficial fluid flow rates of 2, 5, 10 or more times the flow rate of the fluidized bed at incipient fluidization in the absence of the magnetic fluid, along with the substantial absence of gross solids backmixing and fluid bypassing such as bubbling in gas fluidized beds and roll-cell behavior in liquid fluidized beds. As the superficial fluid velocity is increased, the pressure drop through the bed is similar to that which would be expected from a normal fluidized bed not subjected to an applied magnetic field—the pressure drop increases to a value corresponding to the ratio of bed weight to cross sectional area at the minimum fluidization velocity, and then remains relatively constant as the fluid velocity is increased. This stably fluidized bed condition persists even as the solids are continuously added to and removed from the contacting vessel.

The magnetically stabilized fluidized bed (MSB) thus described combines in one system the principal advantages of both fluidized bed and fixed bed reactor systems as is summarized in Table I below.

TABLE I

|  | Fluid Bed | MSB | Fixed Bed |
| --- | --- | --- | --- |
| Small particle size with low $\Delta p$ | yes | yes | no |
| Absence of fluid bypassing | no | yes | yes |
| Continuous solids throughput | yes | yes | no |
| Avoids solids backmixing | no | yes | yes |
| Avoids entrainment from bed | no | yes | yes |

As an example of the advantage of a magnetically stabilized bed, the use of small particle size reduces diffusional resistance within a bed particle such that the particle can be used more effectively. At the same time, both high pressure drop due to the use of small particles and gross fluid bypassing are eliminated. The use of small particles in the sorption process permits a faster transfer of the sorbed species from the fluid than do larger adsorbent particles, thereby enabling a faster approach to equilibrium. An additional advantage is that the solids can be added to and removed from the bed, and that backmixing of solids in the bed will be minimized or eliminated such that said solids move in a plug flow manner from near the point of introduction to near the point of withdrawal.

For economy, it is desirable that the bed solids achieve sufficient magnetization to stabilize the bed at a relatively small intensity of applied magnetic field. When ferromagnetic particles are placed in the magnetic field, the induced magnetization is a function of the magnetic material, the geometry of the ferromagnetic particle and the geometry of the bed, as is described in U.S. Pat. No. 4,247,987.

Conventional permanent magnets, electromagnets or both can be employed to provide the magnetic field. The electromagnets may be energized by alternating or direct current, although direct current energized magnetic fields are preferred. When powered by direct current with the use of solid state control or a transformer/rectifier, electromagnets are particularly desirable for applying a magnetic field to the bed particles and provide an excellent method of stabilizing the fluidization of the bed particles in response to the flow of the carrier fluid.

The invention is not limited by the shape or positioning of the magnet employed to produce an externally applied magnetic field. The magnet can be of any size, strength or shape and can be placed above or below the bed depending upon the solids used, the degree of stabilization required and the like. The magnets can be placed within or outside the contacting vessel and may even be employed as an integral portion of the vessel structure. The process is not limited to any particular vessel or vessel material and it can be readily adapted for use in contacting vessels currently employed by industry. In a preferred embodiment of the present invention, a solenoidal shaped electromagnet is employed to surround the fluidized bed as this provides the most uniform magnetic field and consequently the best stability throughout the bed.

With proper selection of magnetic particles, the power requirement for the electromagnet field source in commercial plants will be modest. Magnet power dissipation generates heat that may be removed using natural convection air cooling. This eliminates any need for liquid convection cooling and attendant requirements for coolant treatment and recirculation. The magnetic field source may be computer designed with high confidence to yield an applied magnetic field having a specified intensity and uniformity.

The strength of the magnetic field to be applied to the fluidized solids in the contacting zone will depend on the magnetization of the magnetizable particles and the degree of stabilization desired. Particles having relatively weak magnetic properties, e.g., some composites and alloys, will require the application of a stronger magnetic field than particulate solids having strong magnetic properties, e.g., iron, to achieve similar stabilization effects. The size and shape of the solids will also have an effect on the strength of the magnetic field to be employed. The magnetization of the particles should not be sufficient to cause excessive particle to particle attractive forces and agglomeration which would tend to freeze or lock the particles in the bed and prevent continuous operation. However, since the strength of the field produced by an electromagnet depends on the current strength of the electromagnet, an operator can readily adjust the field strength to achieve the desired degree of stabilization for the particular system employed. Specific methods of applying the magnetic field are also described in U.S. Pat. Nos. 3,440,731; 3,439,899; 4,115,927 and 4,143,469; British Pat. No. 1,148,513 and in the published literature, e.g., M. V. Filippov, Applied Magnetohydrodynamics, *Trudy Instituta Fizika Akad Nauk.*, Latviiskoi SSR 12:215-236 (1960); Ivanov et al, *Kinet. Kavel,* 11 (5): 1214-1219 (1970); Ivanov et al, *Zhuranal Prikladnoi Khimii,* 45:248-252 (1972); and R. E. Rosensweig, *Science,* 204:57-6 (1979), the disclosures of which are incorporated herein by reference. The most preferred applied magnetic field will be a uniform magnetic field such as is described in U.S. Pat. No. 4,115,927. Typically, the applied magnetic field for an empty vessel will range from about 5 to about 1500 Oersteds, preferably from about 10 to about 1000 Oersteds.

The present invention can be utilized in a wide variety of processing configurations. For example, after undergoing the continuous transverse flow contacting described previously, the magnetizable particles may be removed from the contacting vessel, although the removal may be intermittent. If desired, the bed particles may be recycled to the contacting vessel or be passed through said vessel in a single pass mode. As an example of another configuration, the magnetizable particles may be removed continuously (or intermittently) from a first contacting vessel and passed to a second contacting vessel for regeneration prior to being recycled to the first contacting vessel. These examples should be considered as illustrative only and are not to be construed as limiting the scope of the present invention.

The operating conditions employed in the present invention may vary broadly depending on the particular mixture being separated, the adsorbent being used, etc., and will include those typically employed in sorption processes. In general, the contact time of the feed mixture with the adsorbent need only be for a period of time necessary to separate at least a portion of the components therefrom. Temperatures will range from ambient, or lower, to the Curie temperature of the magnetic component within the bed, and pressures will range from about 1 to about 10,000 psia. The superficial fluid velocity of the carrier fluid will range between $U_{mf}$ and $U_T$ and will vary depending on the type of solids in the bed, the geometry of the vessel and the like. Normally, however, the superficial fluid velocity will range from about 0.0001 to about 5 m/sec. Liquid phase superficial fluid velocities will range typically from 0.0001 to about 0.1 m/sec. while gas phase superficial fluid velocities will range from about 0.001 to 5 m/sec. Preferably, the bed particles move in a plug flow manner crossflow (i.e. perpendicular) to the ascending fluid mixture which comprises the feed mixture and the carrier fluid. Similarly, the solids transverse flow velocity can vary broadly depending upon the velocity of the fluid mixture, the geometry of the vessel, the solids being fluidized, the components in the feed mixture being separated and other operating parameters. Generally, however, the solids velocity will range from about 0.001 to about 50 cm/sec.

In a preferred embodiment, all components of the mixture will be recovered from the transverse flowing bed in a single vessel. However under some circumstances, residual components remaining on the adsorbent may be desorbed in a subsequent operation in another vessel by any one of the three known methods, i.e., thermal swing, pressure swing or purge cycle. The thermal swing process involves heating the particles to a temperature where the adsorptive capacity for the particular component is reduced to a low level. The component is then easily removed by a purge gas stream. The pressure swing process involves reducing the beds total pressure and thereby the component partial pressure during desorption to reduce the particle's adsorption capacity while the bed temperature is held constant. The purge cycle process involves using another fluid during desorption to either strip or displace the adsorbed component from the adsorbent. Various known purging agents may be used, e.g., hydrogen gas, ammonia, steam, hydrocarbon gases, etc.

Figure 1:
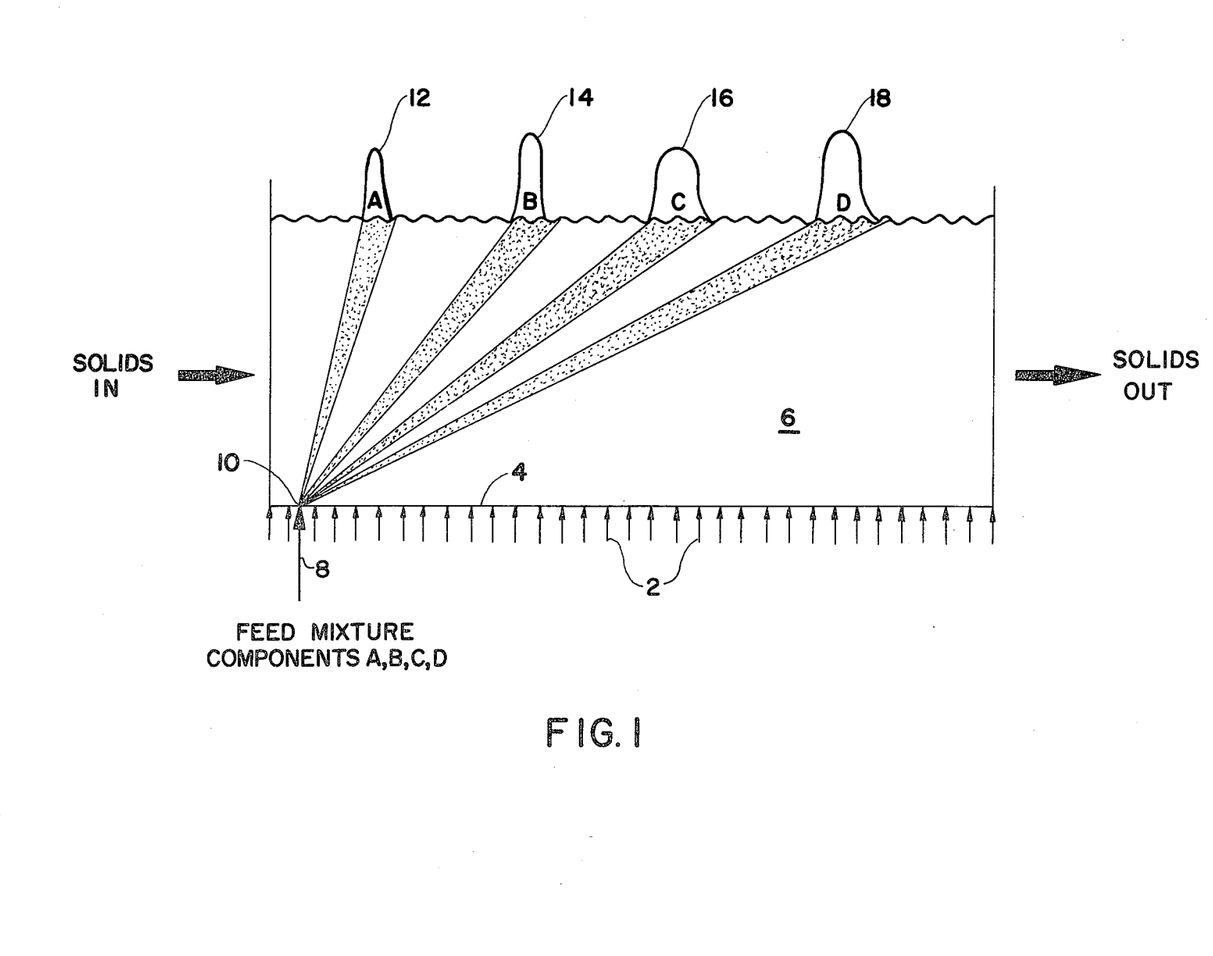
FIG. 1 illustrates the use of a transverse flow magnetically stabilized fluidized bed in continuous chromatographic separations.

This invention may be best described by reference to FIG. 1 which illustrates the use of the present invention to separate a feed mixture into its components. As shown therein, a vertically flowing carrier fluid 2 passes continuously through a distributor 4 and fluidizes a magnetically stabilized fluidized bed 6 containing solid adsorbents that flow perpendicular (i.e., crossflow) to the carrier fluid. The distributor is located in the lower part of the bed and, typically, supports said bed. Although the solids flow need not be perpendicular to the flow of the carrier fluid, such is preferred to obtain a more efficient separation. Typically the distributor or bed tilt angle (i.e. the angle of the distributor relative to the horizontal) will be less than 45 degrees, preferably less than 30 degrees and most preferably less than 20 degrees. The carrier fluid may be gaseous or liquid. A feed mixture 8 having components A through D is introduced into bed 6 at injection point 10. Each component of the mixture has different adsorption-desorption characteristics with respect to the solid adsorbent. In this illustration, component A is least strongly adsorbed by the adsorbent while components B, C, and D are more strongly adsorbed. Each component moves through the bed due to the upward flow of the carrier fluid and the transverse flow of bed solids. Thus, each component has a velocity vector in two directions—one is in the direction of solids movement due to adsorption thereon while the other is in the direction of the carrier fluid toward the upper surface of the bed due to desorption of the components from the solids. The point at which a particular component exits from the upper surface of the bed depends upon several factors including the transverse flow velocity of the bed solids, the velocity of the carrier fluid and the adsorption-desorption characteristics of the bed solids. For example, the weakest adsorbed component (component A) is not transported significantly by the moving solids and exits (along with a portion of the carrier fluid) from the upper surface of the bed at location 12 close to the injection point of the feed mixture. The more strongly adsorbed components (components B, C and D) pass further downstream with the adsorbent solid and, consequently, exit (along with a portion of the carrier gas) from the upper surface of the bed further from the feed injection point at locations 14, 16 and 18. Components A through D in mixture with the carrier fluid are then recovered from the upper surface of the bed at different distances downstream from the injection point.

The present invention can also be modified in a variety of ways to facilitate the chromatographic separation of a feed mixture. For example, not all separations produce product streams comprising a portion of the carrier gas and a portion of the feed mixture consisting essentially of one component of the feed mixture as is shown in FIG. 1. Depending on the composition of the feed mixture, it may be difficult if not impossible to obtain complete resolution of the components into separate product streams, i.e., there may be overlap of adjacent components such as is disclosed in U.S. Pat. No. 3,494,104, the disclosure of which is incorporated herein by reference. In addition, resolution is decreased at increased throughput rates. However, improved resolution and component separation may be obtained by recycling to the feed mixture at least a portion of the product streams that contain overlapping components.

The present invention may also be modified to permit progressive change in temperature as the bed solids move through the contacting vessel. Differentially heating one or more sections of the bed can be achieved by placing resistance wire or other heating elements within or outside the contacting vessel (or including them as an integral part of the vessel structure), by introducing carrier fluid at different temperatures into one or more sections of the bed, or by a combination of both methods. Non-isothermal conditions enable better control of the separation by permitting the selection of the appropriate temperature for each component fraction (which results in improved separation of each fraction) and reduces the time required to separate the components. Temperature programming in connection with conventional chromatographic separations is discussed in McNair, H. M., *Chromatography*, 3rd Edition, Ed: E. Heftmann, Van Nostrand Reinhold (1975) the entire disclosure of which is incorporated herein by reference.

Another modification relates to effecting a three dimensional separation of a feed mixture (rather than the two dimensional separation discussed in FIG. 1) by applying an electric field in a direction transverse (i.e., non-parallel) to the flow of both the carrier fluid and the bed solids. Each component of the feed mixture has different electrical mobilities which cause each component to move at different velocities in the direction of the electrical field. Therefore, when the direction of the field is non-parallel to both the flow of the carrier fluid and of the bed solids, each component will have a velocity vector in three directions: one is in the direction of solids movement due to adsorption thereon, another is in the direction of the carrier fluid toward the upper surface of the bed due to desorption of the components from the solids and another is in the direction of the applied electric field.

Figures 2A, 2B, 2C, 2D:
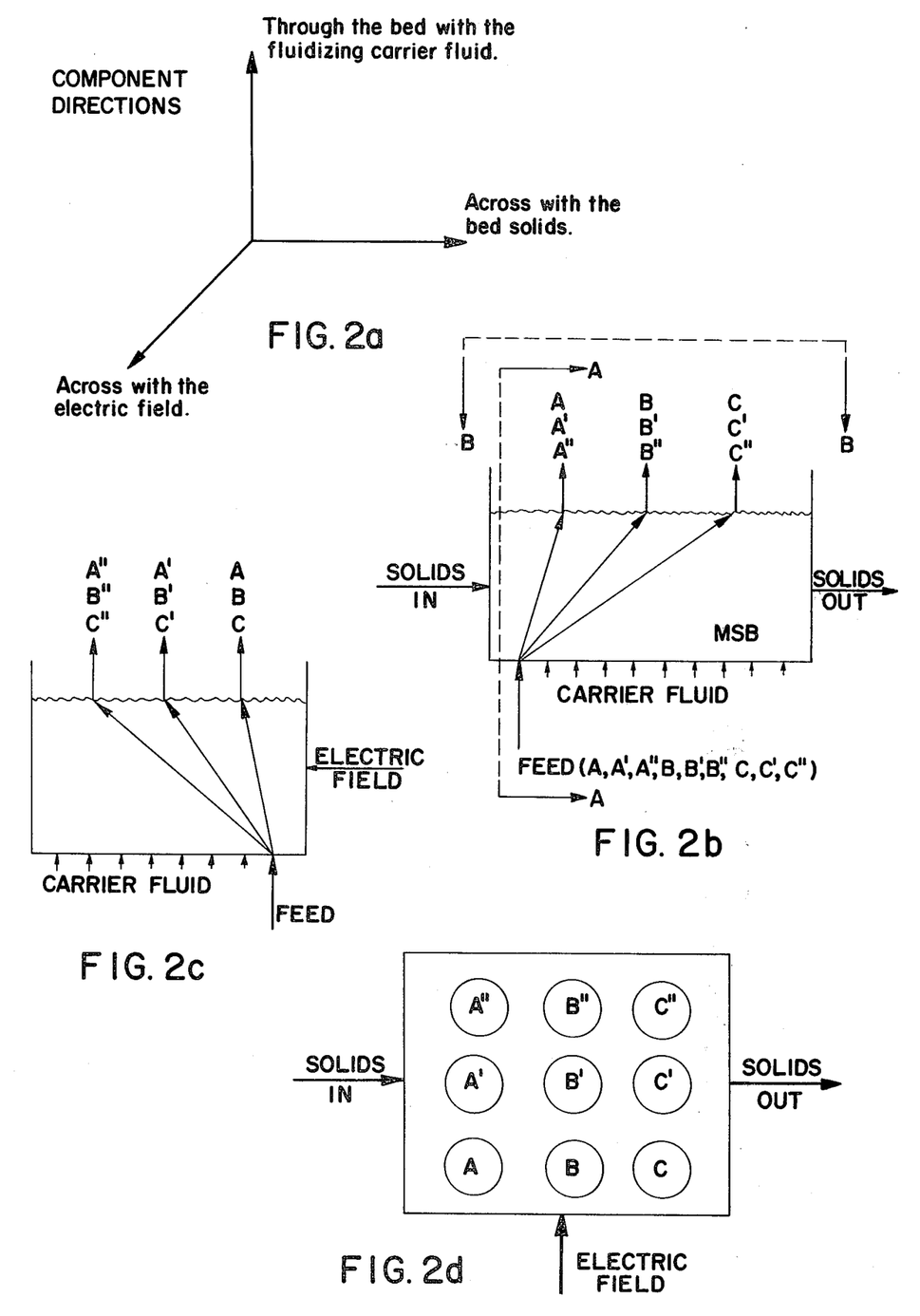
FIG. 2a–2d illustrates a modification of a transverse flow magnetically stabilized fluidized bed when used in continuous chromatographic separations.

The three dimensional continuous chromatographic separation of a feed mixture can be better understood by referring to FIG. 2 which contains parts 2a–2d. FIG. 2a shows the direction of the three velocity vectors for the components of a feed mixture. FIG. 2b illustrates the two dimensional continuous chromatographic separation of a feed mixture containing nine components (A, A', A'', B, B', B'', C, C' and C'') in a magnetically stabilized bed similar to that shown in FIG. 1 wherein bed solids are moving crossflow to the carrier fluid. For the purpose of illustration, assume that the components of the feed mixture are in three classes (A, B and C) in order of increasing adsorptivity and that the components of each class (A, A' and A'') have identical sorption characteristics but different electrical velocities. As such, the components of the feed mixture undergo a two dimensional separation by class (i.e., A, B and C) but the components in each class will not be separated. FIG. 2c is a side view of FIG. 2b cut along section A—A and illustrates the effect of an applied electric field that is nonparallel to the flow of the carrier fluid and the bed solids. Since the components in each class have different electrical mobilities and thus move in the direction of the electric field at different velocities, components having identical adsorption characteristics will be separated by electrochromatography at the same time components with identical electrical mobilities will be separated by adsorption chromatography. The final arrangement of the nine components following the three dimensional separation described above is shown in FIG. 2d which is a top view of FIG. 2b cut along section B—B. The use of an electric field to separate mixtures according to the electrical mobilities of the components is discussed in U.S. Pat. No. 3,449,938, the entire disclosure of which is incoporated herein by reference.

Yet another modification involves effecting chemical reactions simultaneous with the present chromatographic separation process. By using the present invention to separate and remove the reaction products from a reacting mixture, undesirable reverse reactions may be minimized or prevented and enhanced yields obtained, particularly when the thermodynamic equilibrium is unfavorable. (See Magee, E. M., *I&EC Fundam.*, 2 32 (1963) and Gaziev, et al., *Kinet Katal*, 4, 688 (1963) for early proposals of chromatographic reactors, and Cho, B. K. et al., *Chem. Eng. Sci.*, 35, 74 (1980) for application of chromatographic reactors to mechanically rotated transverse flow devices.)

The present invention may also be modified to permit a variation of the elution chromatography process described in U.S. Pat. No. 4,001,111, the entire disclosure of which is incorporated herein by reference. As disclosed therein, the liquid phase separation of two or more components from a feed mixture may be obtained by injecting a feed mixture and carrier fluid plus eluent sequentially into a column. If the feed components have different distribution coefficients, there will result a separation of the components thereof due to a differential migration of said components according to their distribution between two phases. By use of the present invention, the liquid phase separation of two or more components of a feed mixture may be obtained while injecting a different carrier fluid or changing the concentration of the carrier fluid at varying distance from the feed injection point. In addition, a decrease in tailing of the product peaks as well as a reduction in the size of the separation vessel and volume of eluent may be obtained by (1) increasing the eluent concentration in the carrier-eluent in a stepwise manner with distance from the feed point, (2) continuously increasing the eluent concentration in the carrier-eluent with distance from the feed point as the feed passes through the bed and (3) substituting a strong eluent for a weak eluent during elution of the feed components.

This invention will be further understood by reference to the following examples which are not intended to restrict the scope of the claims appended hereto.

EXAMPLE 1

Figure 3:
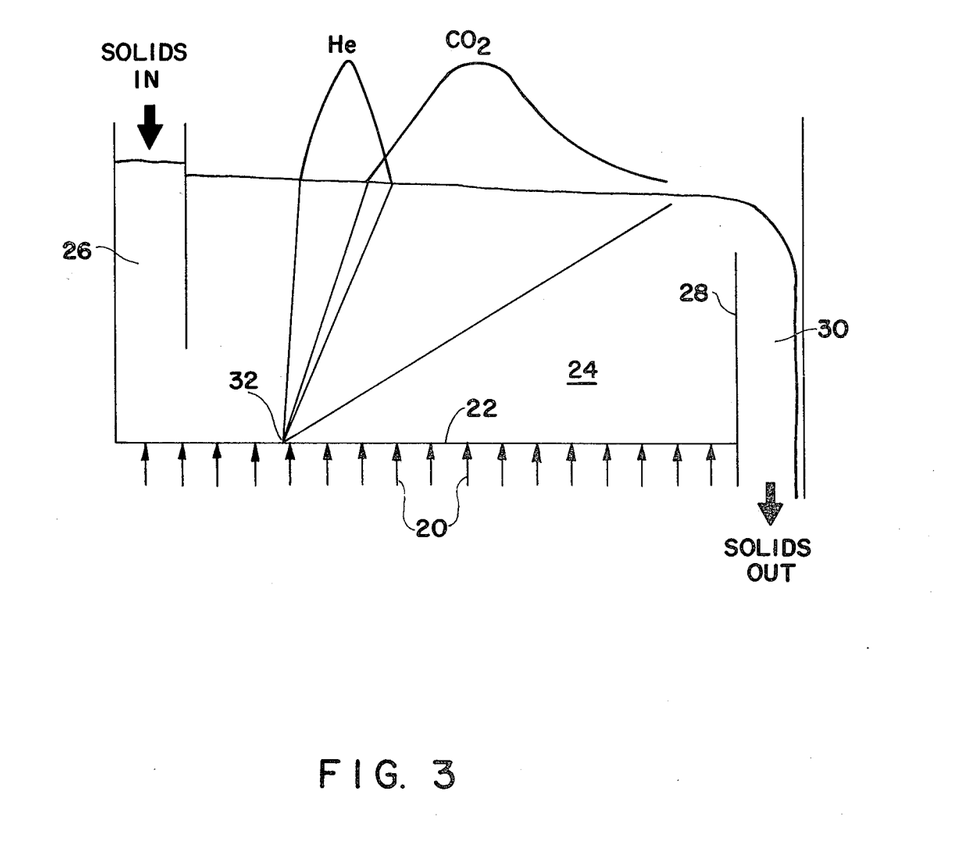
FIG. 3 illustrates continuous chromatographic separation of helium and carbon dioxide using a transverse flow magnetically stabilized fluidized bed.

The experimental apparatus used to demonstrate the operation of continuous chromatographic separations in a magnetically stabilized bed is shown in FIG. 3. As shown therein, fluidizing air 20 is injected continuously through a porous bronze distributor grid 22 as solids move continuously crossflow to the air flow. The solids are added to the bed 24 through a channel 26 on the left side, pass in plug flow to the right, over and through a weir 28, and exit the bed through a one inch long space 30 at the end of the grid. The length of the bed in the solids flow direction is approximately 69 cm and the bed width is 7.62 cm. The grid is divided into two sections, each about 34.5 cm long, which are supplied independently with fluidizing air. The solids are −20 +60 U.S. sieve 70 wt. % stainless steel/alumina composite.

The magnetic field is produced by two solenoidal electromagnets connected in parallel, placed one above the other 15.5 cm apart, surrounding the crossflow bed. The magnets are elliptical in design with inside dimensions of approximately 30 cm × 105 cm. Each is made of 508 turns of #8 enameled copper wire.

Runs were made using a superficial fluidizing air velocity of 30.3 cm/sec, a bed solids crossflow velocity of 0.56 cm/sec, a bed height of 14 cm, and an applied magnetic field of 191.7 Oersted. Trace quantities of He and $CO_2$ were introduced at injection point 32 through a 0.32 cm O.D., 0.16 cm I.D. copper tube.

Figure 4:
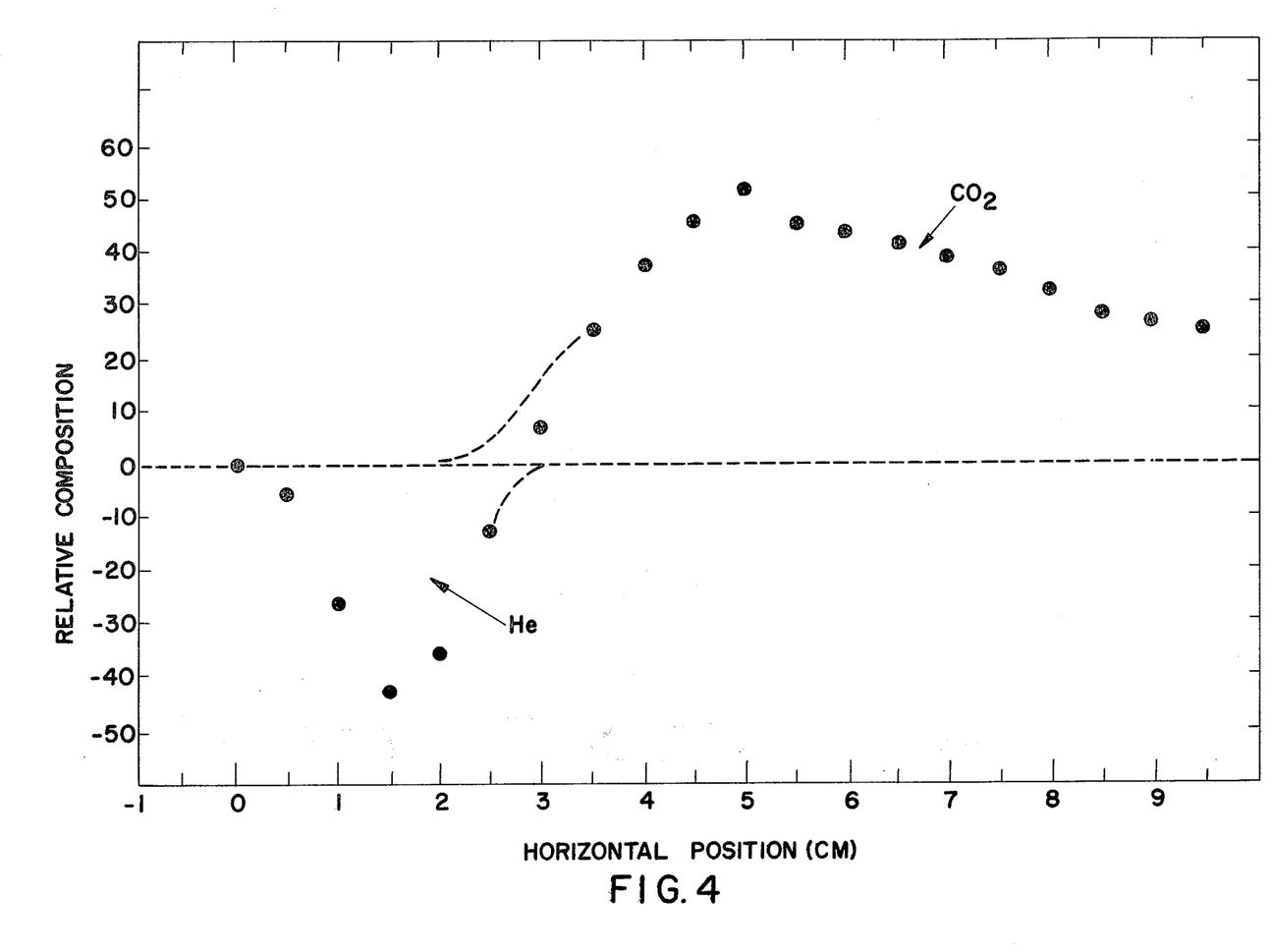
FIG. 4 shows the experimental results for the continuous chromatographic separation of helium and carbon dioxide in a transverse flow magnetically stabilized fluidized bed.

The concentration of each component was measured by passing the sample tube of a Matheson "leakmeter" (which measures thermal conductivity) along the top surface of bed 24 parallel to the solids flow. Runs were made for each component individually and for the simultaneous injection of both components. Helium caused a negative deflection of the concentration meter while $CO_2$ caused a positive deflection. The $CO_2$ was adsorbed more strongly by the alumina and passed vertically through the bed more slowly than He and thus exited from the top surface of bed 24 further downstream from the injection point than where He exited. The results from a run in which both He and $CO_2$ were simultaneously and continuously injected into a crossflow MSB are shown in FIG. 4.

EXAMPLE 2

Separation of Three Normal Paraffins

Using the apparatus described in Example 1 and certain normal paraffins as the feed, experiments were conducted to determine if for light loadings the location of the component peaks when separating a mixture was the same as when the components were injected individually. Methane, n-butane, and n-pentane were the normal paraffins selected for this experiment. The detection system employed was a flame ionization detector with a millivolt output connected to a strip chart recorder. The detector had a delay time of about 2 seconds. The chart speed was b 5.08 cm/min. and the detector probe moved along the top surface of the bed in the direction of solids flow at 0.085 cm/sec.

The runs were made using a superficial fluidizing air velocity of 34.8 cm/sec, a bed solids crossflow velocity of 0.513 cm/sec, a bed height of 14 cm, and an applied magnetic field of about 200 Oersted. The methane and n-butane were available as gases from cylinders. The n-pentane gas was produced using liquid n-pentane and passing argon gas through a bubble column.

Figure 5:
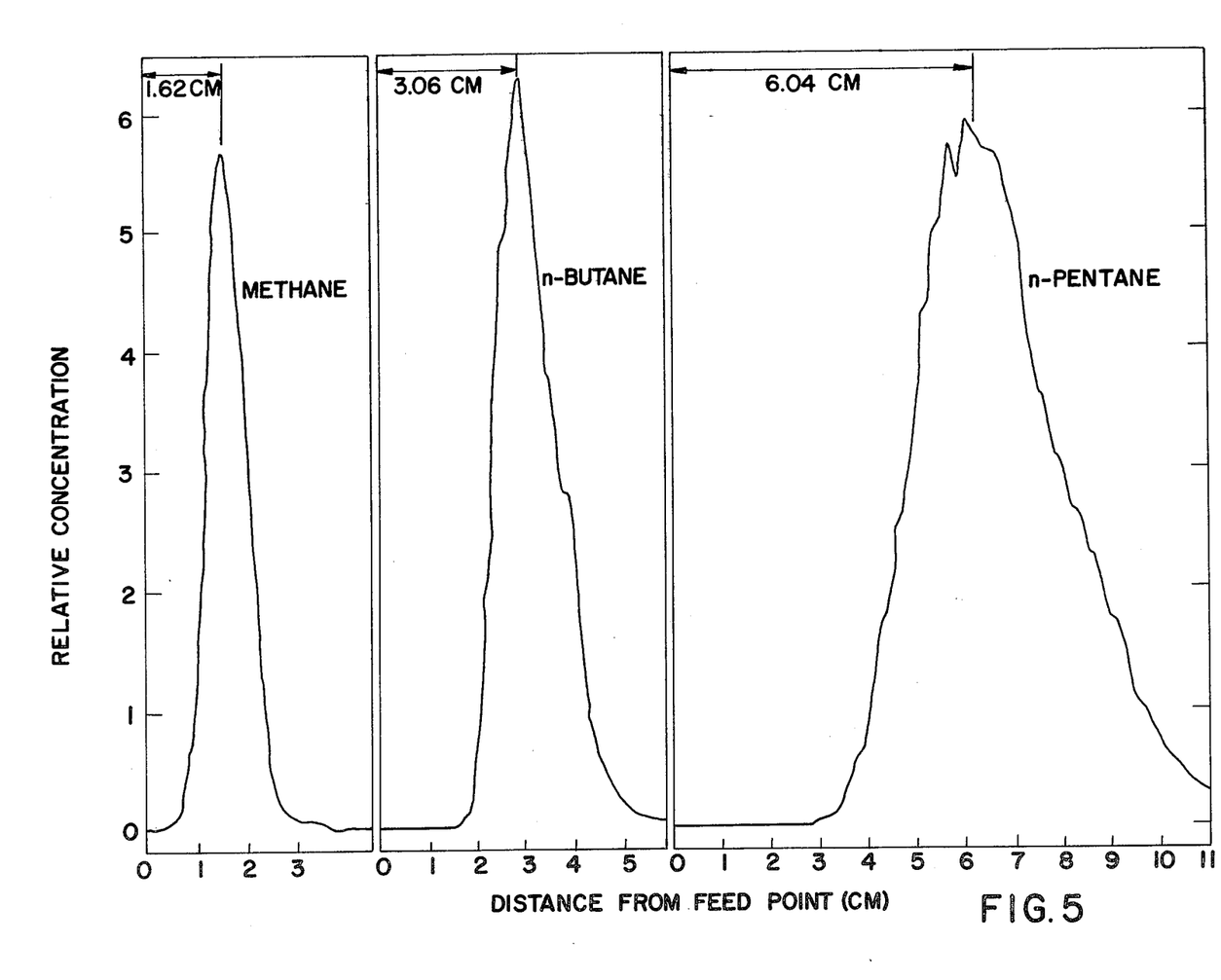
FIG. 5 shows the elution curves of methane, n-butane and n-pentane in a transverse flow magnetically stabilized fluidized bed.
Figure 6:
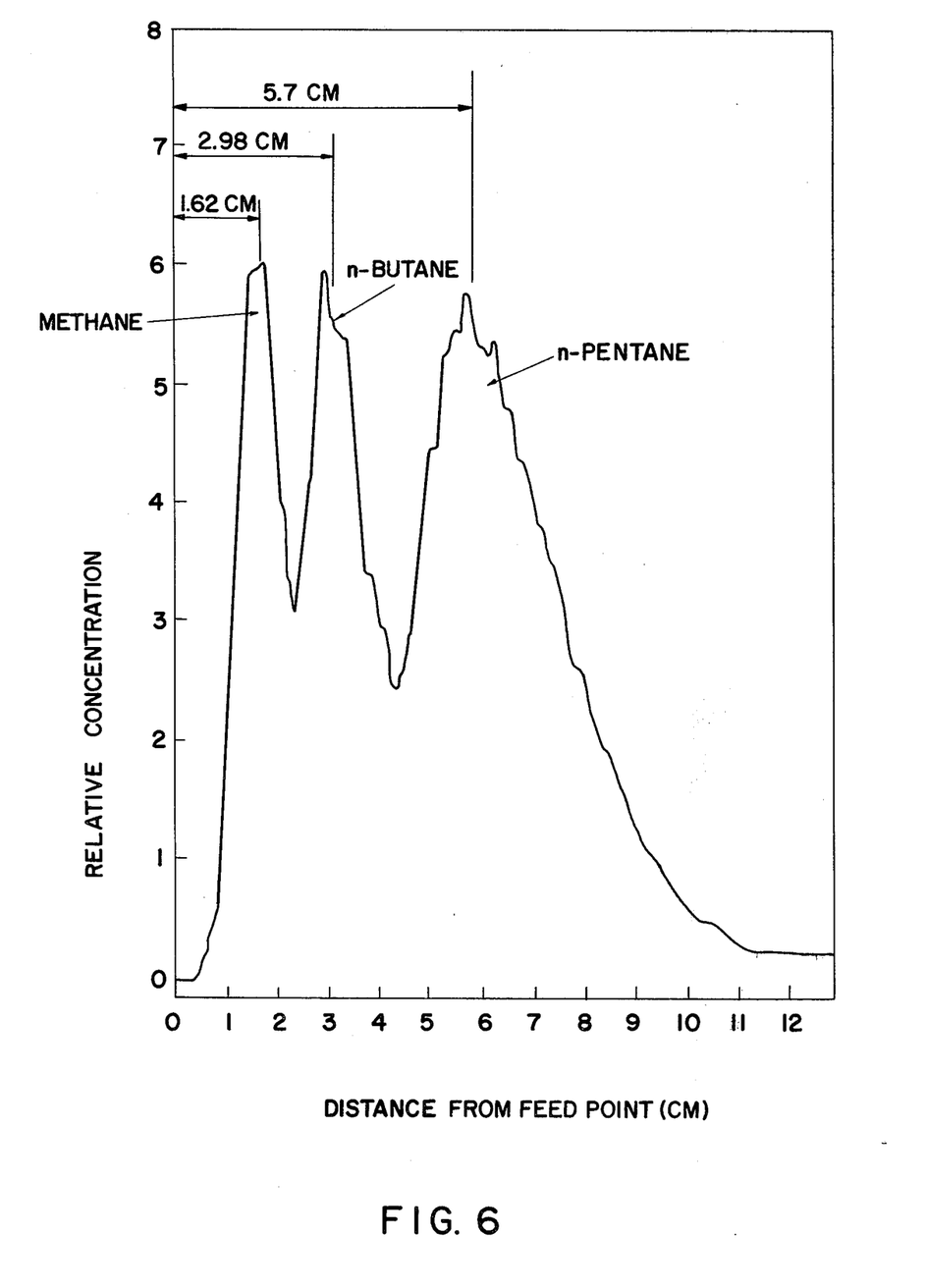
FIG. 6 shows the elution curves of a mixture of methane, n-butane and n-pentane in a transverse flow magnetically stabilized fluidized bed.

FIG. 5 shows the elution curves of the individual normal paraffins while FIG. 6 shows the elution curve for the paraffin mixture. Comparison of the two figures indicates that the elution position of the components when injected into the bed as a mixture are nearly the same as when they were injected individually.

EXAMPLE 3

Separation of Five Normal Paraffins

This example illustrates the continuous crossflow MSB chromatographic separation of five normal paraffins using the apparatus described in Example 1 and the detection system described in Example 2. The five normal paraffins used were methane, n-butane, n-pentane, n-hexane, and n-heptane. The run was made with a superficial fluidizing air velocity of 35.9 cm/sec, a bed solids crossflow velocity of 0.54 cm/sec, a bed height of 14 cm, and an applied magnetic field of about 200 Oersted. The recorder chart speed was 2.54 cm/min. As in Example 2, the methane and n-butane were available as gases from cylinders. The n-pentane, n-hexane, and n-heptane gases were produced using argon gas passed through a bubble column.

Figure 7:
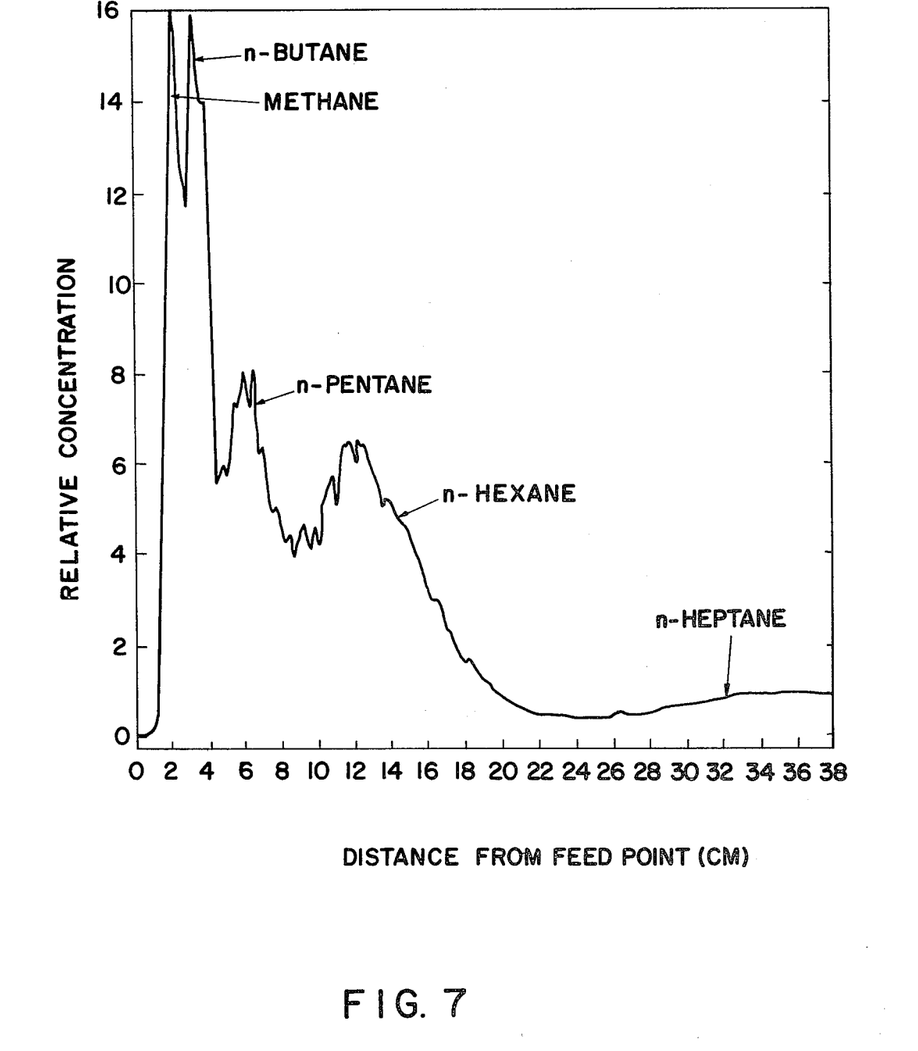
FIG. 7 shows the continuous chromatographic separation of a mixture of methane, n-butane, n-pentane, n-hexane and n-heptane in a transverse flow magnetically stabilized fluidized bed.

The crossflow MSB chromatogram from the continuous injection of the five normal paraffins is shown in FIG. 7. Tests with the individual components (not shown) indicate elution positions to be nearly the same for the mixture as compared to the individual component runs.

EXAMPLE 4

Effect of Increasing Bed Height

Example 2 was repeated using a bed height of 22 cm, a superficial fluidizing air velocity of 35.2 cm/sec and a bed solids crossflow velocity of about 0.5 cm/sec.

Figure 8:
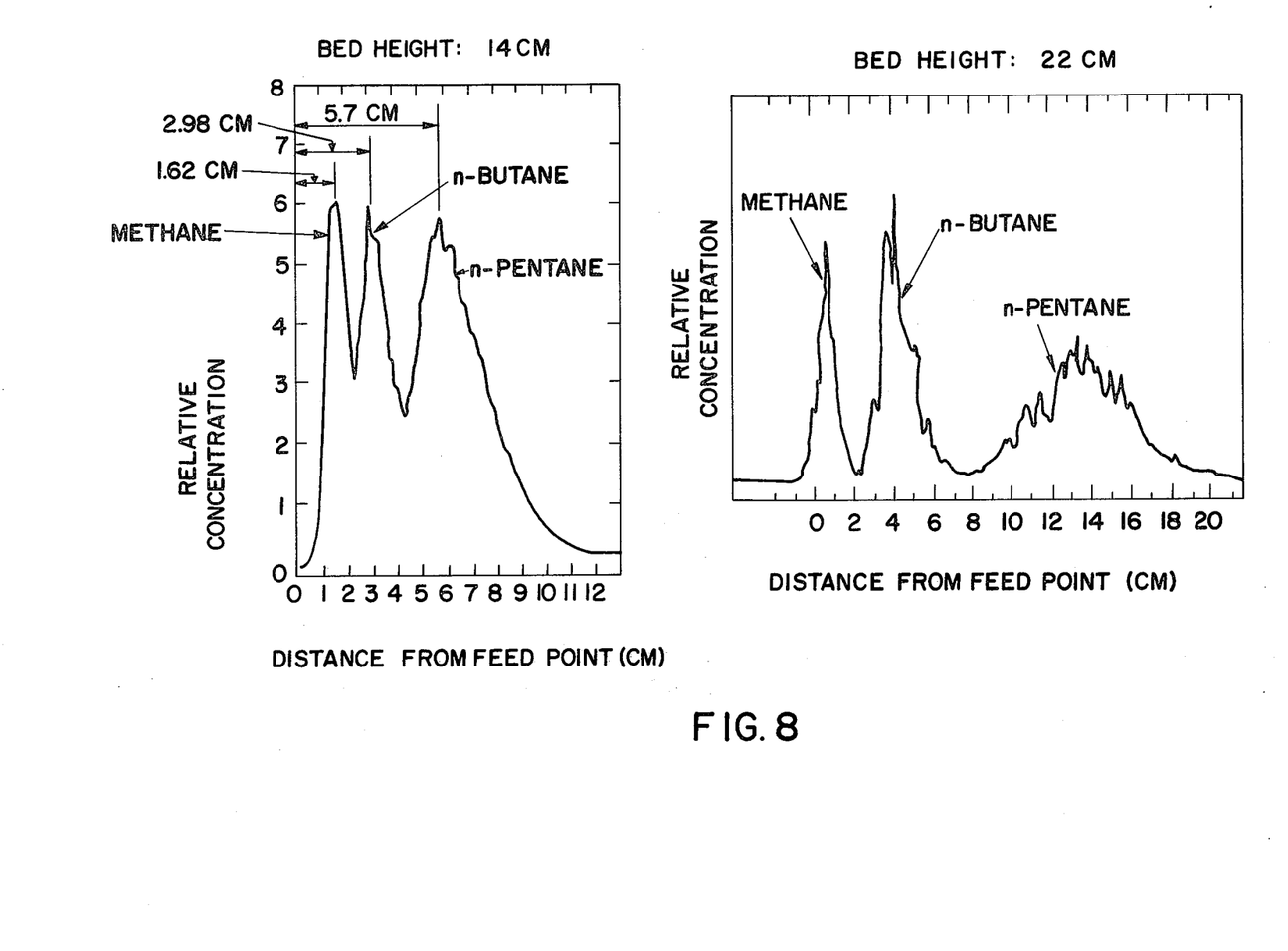
FIG. 8 shows the effect of increased bed height in a transverse flow magnetically stabilized fluidized bed.

FIG. 8 illustrates the results using bed heights of 14 cm (shown in FIG. 6) and 22 cm. As shown therein, improved resolution of adjacent product peaks (i.e., improved separation of the feed components) is obtained by increasing bed height.

What is claimed is:

1. A chromatographic process for continuously separating a feed mixture containing at least two components which comprises:
   (a) introducing said mixture into a moving bed containing magnetizable particles, said bed being fluidized by a carrier fluid distributed along said bed and passing through said bed in an ascending manner transverse to the flow of said bed and being stabilized by a magnetic means having sufficient strength to suppress solids backmixing therein,
   (b) contacting said mixture with an adsorbent in said bed for a period of time necessary to chromatographically separate at least a portion of one of said components from said mixture,
   (c) recovering at least two streams, at least one of which is a product stream from said moving bed along the path of said bed, said product stream comprising a portion of the carrier fluid and a portion of the feed mixture containing at least a portion of one of said components.

2. The process of claim 1 wherein said magnetizable particles are composites of non-ferromagnetic material, ferromagnetic material, ferrimagnetic material or mixtures thereof.

3. The process of claim 1 wherein said magnetizable particles are admixed with non-ferromagnetic particles.

4. The process of claim 2 or 3 wherein the non-ferromagnetic material, ferromagnetic material, ferrimagnetic material or mixtures thereof has sorption properties.

5. The process of claim 2 or 3 wherein the non-ferromagnetic material, ferromagnetic material, ferrimagnetic material or mixtures thereof has catalytic properties.

6. The process of claimm 2 or 3 wherein the non-ferromagnetic material is an ion-exchange resin.

7. The process of claim 1 wherein the components of said feed mixture are hydrocarbons.

8. The process of claim 7 wherein hydrogen gas is present in said feed mixture.

9. The process of claim 1, 2 or 3 wherein the magnetic means is an externally applied magnetic field.

10. The process of claim 1, 2 or 3 wherein said magnetic means is a uniform magnetic field applied externally in a direction colinear with the flow of the carrier fluid.

11. The process of claim 1, 2 or 3 wherein said magnetic means is obtained using permanently magnetized particles.

12. The process of claim 1, 2 or 3 wherein the carrier fluid is liquid.

13. The process of claim 1, 2 or 3 wherein the carrier fluid is gaseous.

14. The process of claim 1, 2 or 3 wherein a portion of at least one product stream is recycled to said feed mixture.

15. The process of claim 1, 2 or 3 wherein said particles and adsorbent are differentially heated along the path of said bed.

16. The process of claim 1, 2 or 3 wherein an electrical field is applied to the bed in a direction transverse to the flow of both the carrier fluid and the moving solids.

17. The process of claim 1, 2 or 3 wherein said adsorbent is an inert granular material coated with a liquid adsorbent.

18. The process of claim 1 wherein the carrier fluid is separated from at least one of said product streams.

19. The process of claim 1, 2 or 3 wherein the composition of the carrier fluid varies with distance from the point at which the feed mixture is introduced into said moving bed.

20. The process of claim 1, 2 or 3 wherein the concentration of the carrier fluid varies with distance from the point at which the feed mixture is introduced into said moving bed.

21. The process of claim 1, 2, or 3 wherein a chemical reaction occurs within said moving bed.

22. The process of claim 1, 2 or 3 wherein at least one product stream is recovered from the upper surface of said bed.

23. The process of claim 1, 2 or 3 wherein said carrier fluid passes at an angle of greater than 45 degrees to the flow of said bed.

24. The process of claim 1 wherein said feed mixture is introduced into the lower portion of said bed.

25. A chromatographic process for continuously separating $C_8$ aromatic isomers from a mixture of hydrocarbons which comprises:
(a) introducing said mixture into a moving bed containing magnetizable particles, said bed being fluidized by a carrier fluid distributed along said bed and passing through said bed in an ascending manner transverse to the flow of said bed and being stabilized by a magnetic means having sufficient strength to suppress solids backmixing therein,
(b) contacting said mixture with an adsorbent in said bed for a period of time necessary to chromatographically separate at least a portion of one $C_8$ aromatic isomer from said mixture,
(c) recovering at least two streams, at least one of which is a product stream from said moving bed comprising at least a portion of one $C_8$ aromatic isomer and a portion of said carrier fluid.

26. The process of claim 25 wherein said magnetizable particles are composites of non-ferromagnetic material, ferromagnetic material, ferrimagnetic material or mixtures thereof.

27. The process of claim 25 wherein said magnetizable particles are admixed with non-ferromagnetic particles.

28. The process of claim 26 or 27 wherein the non-ferromagnetic material is a zeolite.

29. The process of claim 26 or 27 wherein the non-ferromagnetic material is a zeolite and the zeolite is a potassium exchanged faujasite.

30. The process of claim 25, 26 or 27 wherein the magnetic means is an externally applied magnetic field.

31. The process of claim 25 wherein said feed mixture is a mixture of $C_8$ aromatics.

32. The process of claim 25 wherein at least one product stream contains p-xylene and a portion of the carrier fluid.

33. The process of claim 25 wherein at least one product stream contains ethyl benzene and a portion of the carrier fluid.

34. The process of claim 25 wherein at least one product stream contains o-xylene and a portion of the carrier fluid.

35. The process of claim 25 wherein at least one product stream contains m-xylene and a portion of the carrier fluid.

* * * * *